United States Patent [19]

Colwill et al.

[11] Patent Number: 4,790,302

[45] Date of Patent: Dec. 13, 1988

[54] METHOD AND APPARATUS FOR FIXING BONE FRACTURES

[76] Inventors: John C. Colwill, 2254 Shawnee, Grand Rapids, Mich. 49506; Kenneth M. Wilson, 1456 Mayfield, Grand Rapids, Mich. 49505

[21] Appl. No.: 60,119

[22] Filed: Jun. 9, 1987

Related U.S. Application Data

[63] Continuation-in-part of Ser. No. 875,072, Jun. 17, 1986, abandoned.

[51] Int. Cl.⁴ .............................................. A61F 5/04
[52] U.S. Cl. ............................ 128/92 YZ; 128/92 YY; 128/92 VL; 128/92 YP; 128/92 YR
[58] Field of Search ........ 128/92 YY, 92 YZ, 92 VL, 128/92 YP, 92 YR

[56] References Cited

U.S. PATENT DOCUMENTS 2,675,801  4/1954  Bambara et al. ............... 128/92 YZ
4,502,475  3/1985  Weigle et al. .................. 128/92 VD
4,566,466  1/1986  Ripple et al. .................. 128/92 VL

FOREIGN PATENT DOCUMENTS 445420  5/1975  U.S.S.R. ......................... 128/92 YP

Primary Examiner—Stephen C. Pellegrino
Assistant Examiner—Colleen Reilly
Attorney, Agent, or Firm—Price, Heneveld, Cooper DeWitt & Litton

[57] ABSTRACT

A method and product for fixing fractures in phalanges provides a plate having a surface configured to substantially conform to the intramedullary cortex. Holes are drilled through the external cortex and intramedullary cortex and apertures formed in the plate are aligned with these holes in the bone. Fasteners are extended in the holes from the external cortex side and are threadably engaged with the apertures to draw the plate into abutting relationship with the intramedullary cortex.

20 Claims, 2 Drawing Sheets

METHOD AND APPARATUS FOR FIXING BONE FRACTURES

This application is a continuation-in-part of U.S. application Ser. No. 875,072, filed June 17, 1986, and now abandoned.

BACKGROUND OF THE INVENTION

This invention pertains to a method and apparatus for fixing bone fractures and in particular to such a method and apparatus for fixing long bone fractures. While it is particularly adapted for use with phalangeal fractures, it may also be used in other long bones.

Of the many techniques that have been developed for fixing transverse bone fractures, none have been satisfactory for fixing such fractures in the phalanges. Several devices such as intramedullary rods and marrow nails have been successfully used on larger bones, such as the leg bones. However, all such devices have significant drawbacks that prevent their uses in smaller bones.

In an intramedullary fixation device disclosed in U.S. Pat. No. 3,709,218 issued to Halloran, the device is driven throughout the length of a femur and occupies the entire intramedullary canal. The rod is inserted at the fracture site and must be driven through the canal, out the upper end of the femur and into the buttock in order to effect insertion. If a compression plate is to be used in association with the intramedullary rod, preformed slots in the rod must be identified by x-ray and holes made through opposing walls of the bone aligned with the slots. Screws are passed through the plate, the rod and both walls of the bone. Such a device would be wholly inappropriate in fixing a phalangeal fracture for apparent reasons.

Due to the intricate balance of tendinous units and the lack of soft tissue coverage in the phalanges, these bones are additionally not particularly suitable for other known fixation techniques such as an external compression plate fastened to the periosteal cortex. The plate interferes with the surrounding soft tissues preventing satisfactory early movement, etc. Although Kirschner wires have been used to adequately control many types of phalangeal fractures, the end of the wire also has a tendency to interfere with the surrounding soft tissue. The wires, additionally, often fail to produce a solid fixation of the fracture, particularly transverse phalangeal fractures. This type of fracture is extremely difficult to fix while allowing early range of motion.

SUMMARY OF THE INVENTION

The present invention provides an intramedullary fracture fixing technique utilizing a plate that has a surface configured to conform to the intramedullary cortex of a phalange or other elongated bone. A pair of holes are drilled through the external cortex and the intramedullary cortex of the bone, one on each side of the fracture site, and apertures are provided in the plate. The plate is inserted into the intramedullary canal and means for aligning the apertures with the holes in the bone are provided. Fasteners are extended directly from the external cortex, into the holes and are engaged with the apertures in order to draw the plate into abutting relationship with the intramedullary cortex.

The advantage of this technique is to allow complete freedom of the tendinous structures to glide without interference from a compression plate, wires or the like on the external cortex. The intramedullary plate can be made small enough in longitudinal cross section to optimize ease of insertion. It may be larger in those cases where more strength is required. The location of the plate on the intramedullary cortex transfers much of the bending motion normally absorbed in the plate to the bone itself. This allows a further reduction in the size of the plate needed and, importantly, early motion of the fractured bone. An absorbable material may be used in constructing the plate. Such biologically absorbable materials have been approved for implantation in human subjects by the U.S. Food and Drug Administration and their absorption would permit gradual transfer of forces back to the bone instead of having the fixation device continuing to shield the bone until the fracture heals completely.

When an absorbable material is used, the requirement for a second procedure to remove the fixation device is avoided. If a nonabsorbable material is used, removal may or may not be necessary depending upon the size of the plate and the material from which it is made. Removal, certainly, will not be mandated by any tendency of the plate to interfere with soft tissue.

The invention, additionally, provides a fixation technique with an improved method for aligning the apertures in the intramedullary plate with the holes formed in the bone that avoids the need for x-rays. Further, the use of an intramedullary plate to fix phalangeal fractures provides for the fasteners to be threadably engaged with the plate rather than the bone wall which is thin and brittle. Although the invention is particularly useful in fixing phalangeal fractures, it may be applied to fixation of fractures in other long bones.

These and other related objects, advantages and features of this invention will become apparent upon review of the following specification in conjunction with the drawings.

DESCRIPTION OF THE PREFERRED EMBODIMENT

Figure 1:
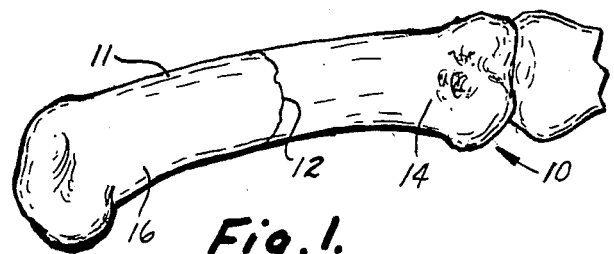
FIG. 1 is a perspective view of a bone, such as a phalange, having a transverse fracture.
Figure 2:
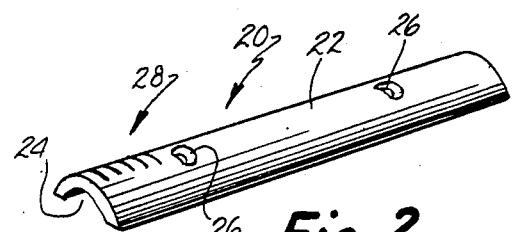
FIG. 2 is an enlarged perspective view of an intramedullary plate according to the invention.

Referring now specifically to the drawings, and the illustrative preferred embodiments depicted therein, an intramedullary plate 20 (FIG. 2) has a convex seating surface 22 that is configured to substantially conform to the contour of the intramedullary cortex, and an opposite nonseating surface 24. A pair of preformed threaded apertures 26 extend between surfaces 22 and 24. A set of marks 28 are spaced longitudinally along seating surface 22 and form a scale, whose function will be explained in detail below.

The first step in the illustrated preferred embodiment of the procedure to fix a phalangeal fracture is to position or overlay the plate 20 on the dorsal periosteal or external cortex with the apertures 26 approximately equally spaced on both sides of the fracture 12. A drill is used to make a hole through the periosteal and intramedullary cortexes of the single wall of the bone at the location of each aperture. A larger diameter drill may be used to slightly countersink the holes at the periosteum. During this drilling portion of the procedure, the identity of the mark 28 that aligns with fracture 12 is noted.

Figure 3:
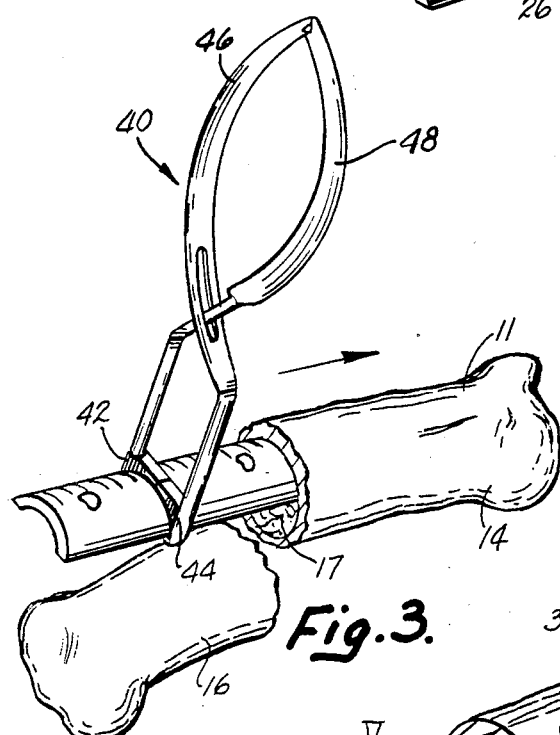
FIG. 3 is a perspective view of a special tool and the procedure used to insert the plate of FIG. 2 into the intramedullary canal.

The portions 14 and 16 of the bone on either side of the fracture are then laterally and/or longitudinally offset as shown in FIG. 3. An applicator 40, having a pair of jaws 42 and 44 configured to the longitudinal cross section of plate 20, is used to guide the plate into the interior or intramedullary cortex of one of the bone portions. Plate 20 is inserted substantially in its entirety into one of the bone portions, illustrated as bone portion 14. With applicator 40 grasping an extreme end of plate 20, bone portions 14 and 16 are longitudinally separated sufficiently to axially align the bone portions on opposite sides of the applicator. The applicator 40 is then utilized to move the plate into the interior second bone portion 16 until the apertures 26 are in alignment with the holes previously drilled into the bone. This can be determined by observing the marks 28 on plate 20 and positioning the plate such that the same mark appears in the fracture site as the one identified as aligned with the fracture during the bone marking and drilling operation.

After the apertures are aligned with the holes in the bone, threaded fasteners 30 are inserted from outside the bone with their stems 34 extending through the holes in the bones and threadably engaging the apertures 26. The applicator 40 is removed, preferably after one fastener has been engaged with its respective aperture 26. The screws are tightened until their heads 32 engage the periosteal cortex and until the plate 20 is drawn snugly against the intramedullary cortex.

Figure 4:
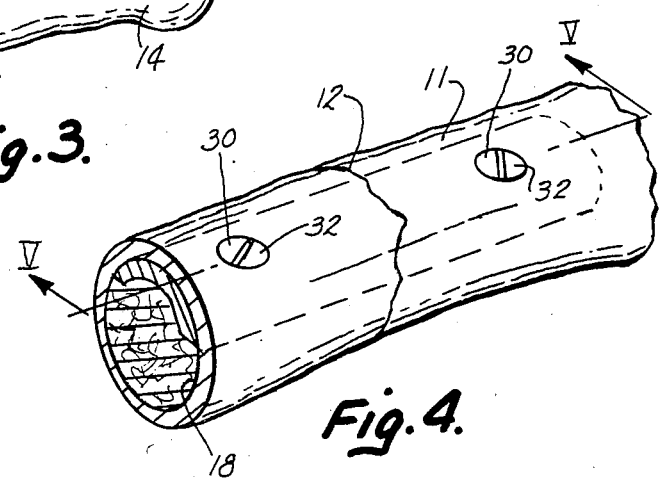
FIG. 4 is a sectioned perspective view showing a transverse fracture in a phalange fixed according to the invention.
Figure 5:
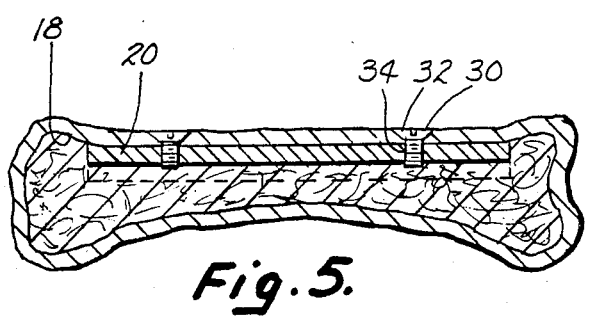
FIG. 5 is a sectioned side elevational view taken along the lines 5—5 in FIG. 4.

As seen in FIG. 4, the only portion of the device to extend outside of the bone is a slight portion of the heads 32 of screws 30. As such, minimum interference with the tendinous units and the blood supply in the periosteum is obtained.

Figure 6:
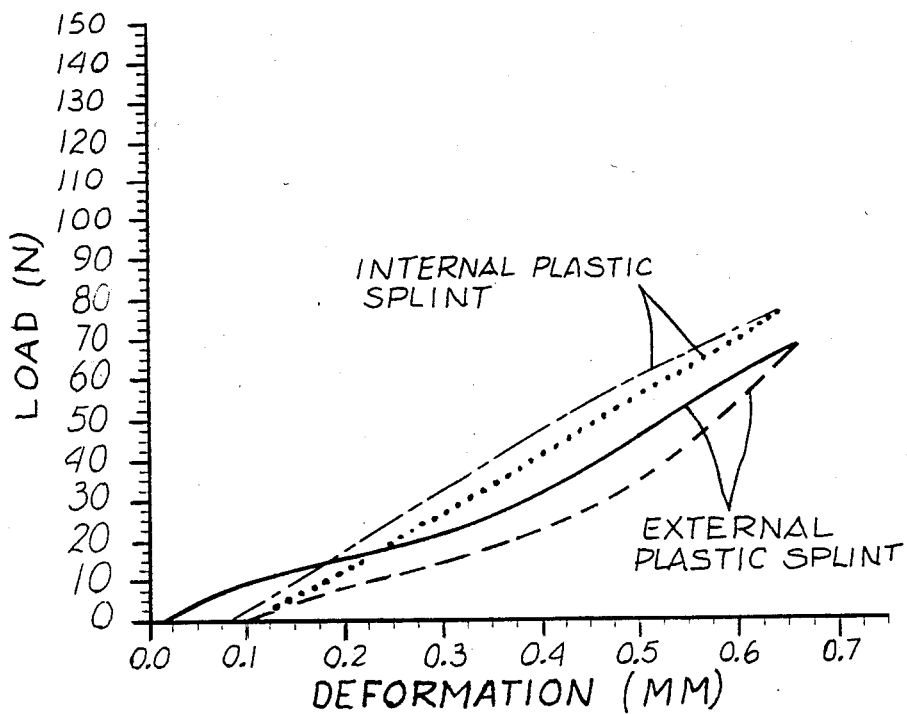
FIG. 6 is a graph depicting the deformation of a simulated bone with a plastic plate or splint placed on the internal surface versus the external surface thereof.
Figure 7:
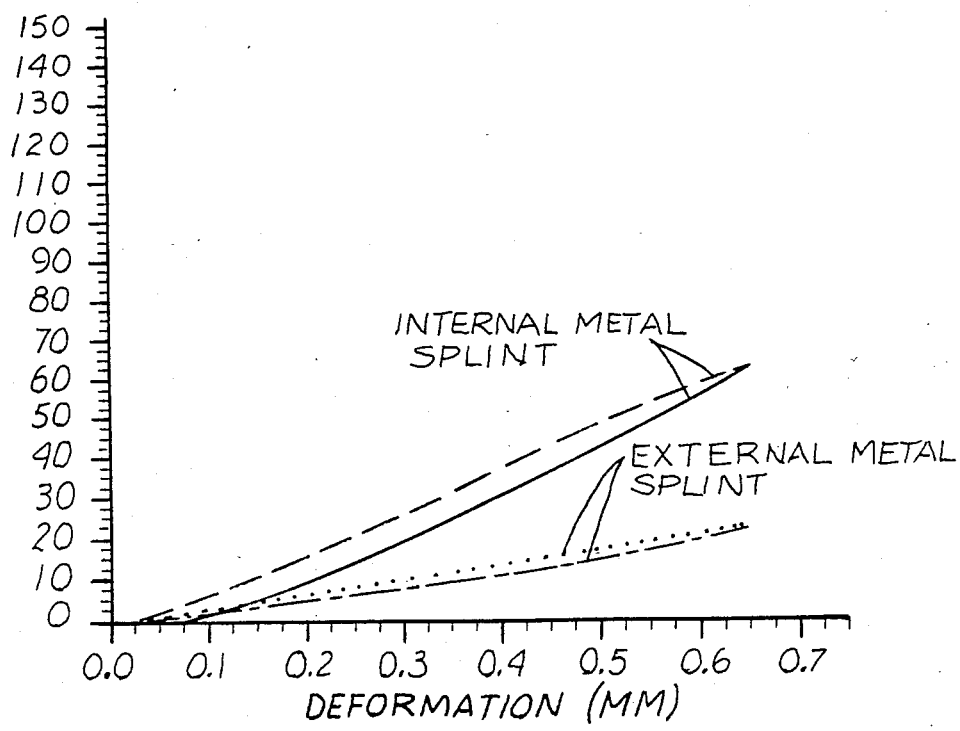
FIG. 7 is the same as FIG. 6 except that a metal plate or splint is used.

FIGS. 6 and 7 depict experimental test results performed in a laboratory to compare the amount of deformation of a simulated fractured bone that is fixed by an internally mounted plate versus an externally mounted plate and that has a pure bending force applied to the simulated bone in the direction of the plate. In FIG. 6 a plastic plate or splint was utilized and in FIG. 7 a metal plate or splint was utilized. The graphs show that, for both the plastic and metal splints, less deformation is experienced, for each amount of load applied to the simulated bone portions, when the plate or splint is internally mounted. The reason for this increased mechanical strength is that the internal splint or plate transfers some of the bending force to the abutting bone segments at the fracture site. In contrast, an external splint or plate directly absorbs all of the bending force and therefore is subject to a greater amount of deformation for a given load. When these results are combined with the additional structural feature of an internal plate, in that the fasteners are threaded into the plate rather than into the bone wall, superior fixation strength is realized.

The increased strength realized by intramedullary plating allows the plate to be made smaller and thus interfere even less with intramedullary blood flow. Further, the increased strength allows the plate to be manufactured from biologically absorbable materials. Such absorbable materials are typically synthetic polymeric materials and can be selected from a group including, for example, hydroxymethacrylate polymer, a polypeptide and a polyglycolic acid but other materials are known. As an example of a nonabsorbable material, titanium has excellent strength characteristics but other materials are suitable. In addition to the plate 20, screws 30 may be made from the absorbable material.

When using the absorbable material for plate 20, the above described procedure may be modified by providing a plate without predrilled apertures. In this procedure, the plate is first inserted into the intramedullary canal, extending approximately equally on both sides of the fracture, and the holes in the bone are drilled. After the bone holes are drilled, the same hole can be utilized to drill and tap the plate in situ by extending the drill and tap through these holes. Alternatively, the plate may be only drilled by extending the drill through the holes in the bone and self-tapping screws used.

This modified procedure is somewhat more simplified and eliminates the need to have a scale to align the openings in the bone and the plate. It is necessary, however, to assure that the thickness of the plate between the surfaces 22 and 24 is sufficient to retain fasteners threaded into the holes drilled into the plate.

Where predrilled and tapped holes 26 are provided in plate 20, the holes are optimally spaced at about 1.2 centimeters apart for middle phalangeal fractures and approximately 1.8 centimeters apart for proximal phalangeal fractures.

Changes and modifications in the specifically described embodiments can be carried out without departing from the scope of the invention. For example, although the procedure was described as applying to the fixing of fractures in phalanges, it could be applied to any elongated bone. In addition, it may be used in combination with other known techniques such as Kirschner wires where multiple fractures are to be fixed. Although the plate has a generally crescent-shaped cross section in the illustrated embodiment, it could, alternatively, have a half-moon or circular cross section. All such variations are within the scope of the invention which is intended to be limited only by the scope of the appended claims.

The embodiments of the invention in which an exclusive property or privilege is claimed are defined as follows:

1. A method of permanently fixing a bone fracture comprising the steps:
   overlaying an elongated plate having two spaced apertures therein on the external cortex of the bone with one said aperture on each side of the fracture, said plate having a convex seating surface abutting the intramedullary cortex;
   drilling a hole in the bone at the location of each said aperture extending from the external cortex to the intramedullary cortex;
   separating the bone portions at the fracture;
   inserting said plate between the bone portions and into the interior of the bone;
   aligning said apertures with said holes;

placing a fastener having a head and a stem into each said hole with the head outside the bone; and locking each said fastener stem into the respective said aperture with said plate abutting the intramedullary cortex;

wherein said plate has a scale comprising a series of longitudinally spaced marks on said seating surface and wherein said step of aligning further comprises locating the plate with the same said mark at the fracture as during said overlaying step.

2. The method in claim 1 further having threads on said fastener stem and said aperture and wherein said step of locking comprises engaging said threads.

3. The method in claim 1 wherein said step of overlaying includes overlaying a plate having apertures that are spaced apart from about 1.2 to about 1.8 cm.

4. The method in claim 3 wherein said step of overlaying includes overlaying a plate that is made from titanium.

5. The method in claim 3 wherein said step of overlaying includes overlaying a plate that is made from a biologically absorbable material.

6. The method in claim 5 wherein said material is a synthetic polymeric material.

7. The method in claim 3 wherein said step of overlaying comprises overlaying said plate on the dorsal external cortex of the bone.

8. A method of permanently fixing a bone fracture comprising the steps:

overlaying an elongated plate having two spaced apertures therein on the external cortex of the bone with one said aperture on each side of the fracture;

drilling a hole in the bone at the location of each said aperture extending from the external cortex to the intramedullary cortex;

separating the bone portions at the fracture;

inserting said plate between the bone portions and into the interior of the bone by grasping said plate by an applicator having a pair of jaws configured to the longitudinal cross section of said plate and inserting said plate substantially entirely into one bone portion and subsequently partially extending the plate into the other bone portion;

aligning said apertures with said holes;

placing a fastener having a head and a stem into each said hole with the head outside the bone; and locking each said fastener stem into the respective said aperture with said plate abutting the intramedullary cortes.

9. A plate for intramedullary fixation of bone fractures comprising:

a body;

a first surface on said body configured to substantially conform to the intramedullary cortex of a bone;

locking means for engaging fasteners extending through the intramedullary cortex; and alignment means for aligning said locking means with holes drilled in a bone;

whereby, said plate that is within the intramedullary canal of a bone, transverse the fracture and made to abut the intramedullary cortex by fasteners extending through the bone external cortex and into said body, will retain the bone portions in rigid relationship;

wherein said locking means comprises apertures in said body and said alignment means comprises a series of marks longitudinally spaced along said first surface.

10. The plate in claim 9 wherein said body is made from titanium.

11. The plate in claim 10 wherein said apertures are spaced apart from about 1.2 to about 1.8 cm.

12. A plate for intramedullary fixation of bone fractures comprising:

a body;

a first surface on said body configured to substantially conform to the intramedullary cortex of a bone;

locking means for engaging fasteners extending through the intramedullary cortex; and alignment means for aligning said locking means with holes drilled in a bone;

whereby, said plate that is within the intramedullary canal of a bone, transverse the fracture and made to abut the intramedullary cortex by fasteners extending through the bone external cortex and into said body, will retain the bone portions in rigid relationship;

wherein said alignment means comprises said plate made from a material capable of having apertures formed therein in situ from a drill extending through holes in a bone and wherein said locking means comprises a second surface on said body opposite said first surface and spaced sufficiently therefrom to provide a sufficiently thick body to retain fasteners threaded into apertures drilled therein.

13. The plate in claim 16 wherein said material comprises a biologically absorbable material.

14. The plate in claim 17 wherein said material is a synthetic polymeric material.

15. A method of fixing a fracture in a bone comprising the steps:

drilling two longitudinally spaced apart holes from the external cortex to the intramedullary cortex on opposite sides of the fracture;

separating the bone portions at the fracture;

inserting an elongated plate having a first surface substantially conforming to the contour of the intramedullary cortex between the bone portions and into the interior of the bone;

providing two apertures in said plate, each aperture aligned with one of said holes in the bone; and placing a fastener having a head and a stem into each said hole with the head outside the bone;

locking each said fastener stem into the respective said aperture with said first surface abutting the intramedullary cortex, whereby only the fastener heads protrude external the bone; and wherein said step of inserting further includes inserting an elongated plate that is made from a biologically absorbable material.

16. The method in claim 15 wherein said material is a synthetic polymeric material.

17. The method in claim 20 wherein said step of placing further includes placing a fastener that is made from a biologically absorbable material.

18. A method of fixing a fracture in a bone comprising the steps:

drilling two longitudinally spaced apart holes from the external cortex to the intramedullary cortex on opposite sides of the fracture;

separating the bone portions at the fracture;

inserting an elongated plate having a first surface substantially conforming to the contour of the intramedullary cortex between the bone portions and into the interior of the bone;

providing two apertures in said plate, each aperture aligned with one of said holes in the bone; and placing a fastener having a head and a stem into each said hole with the head outside the bone; and locking each said fastener stem into the respective said aperture with said first surface abutting the intramedullary cortex, whereby only the fastener heads protrude external the bone;

wherein said step of providing comprises forming said apertures with a drill extending through the holes drilled in a bone.

19. The method in claim 18 wherein said step of providing further comprises tapping threads into said apertures with a tap extending through the holes drilled in a bone.

20. The method in claim 18 wherein said step of placing includes placing a fastener having self-tapping threads.

* * * * *

UNITED STATES PATENT AND TRADEMARK OFFICE
CERTIFICATE OF CORRECTION

PATENT NO. : 4,790,302

DATED : December 13, 1988

INVENTOR(S) : John C. Colwill and Kenneth M. Wilson

It is certified that error appears in the above-identified patent and that said Letters Patent is hereby corrected as shown below:

Column 5, Claim 4, Line 17;

"claim 3" should be --claim 1--;

Column 5, Claim 5, Line 20;

"claim 3" should be --claim 1--;

Column 5, Claim 7, Line 25;

"claim 3" should be --claim 1--;

Column 6, Claim 13, Line 29;

"claim 16" should be --claim 12--;

Column 6, Claim 14, Line 31;

"claim 17" should be --claim 13--;

UNITED STATES PATENT AND TRADEMARK OFFICE
CERTIFICATE OF CORRECTION

PATENT NO. : 4,790,302

DATED : December 13, 1988

INVENTOR(S) : John C. Colwill & Kenneth M. Wilson

It is certified that error appears in the above-identified patent and that said Letters Patent is hereby corrected as shown below:

Column 6, Claim 17, Line 56;

"claim 20" should be --claim 15--;

Signed and Sealed this

Eighth Day of May, 1990

Attest:

HARRY F. MANBECK, JR.

*Attesting Officer*  *Commissioner of Patents and Trademarks*